United States Patent [19]

Conrow et al.

[11] 4,177,209

[45] Dec. 4, 1979

[54] UREYLENEBIS(ANIONIC SUBSTITUTED PHENYLENE CARBONYL)IMINO NAPHTHALENE SULFONIC ACIDS AND NAPHTHALENE CARBOXYLIC ACIDS AND THEIR SALTS

[75] Inventors: Ransom B. Conrow, Pearl River; Seymour Bernstein, New City, both of N.Y.

[73] Assignee: American Cyanamid Company, Stamford, Conn.

[21] Appl. No.: 948,604

[22] Filed: Oct. 4, 1978

Related U.S. Application Data

[62] Division of Ser. No. 778,398, Mar. 17, 1977, Pat. No. 4,129,590.

[51] Int. Cl.$^2$ .................. C07C 143/30; C07C 143/83
[52] U.S. Cl. ....................................... 260/506; 560/13
[58] Field of Search .............. 260/506, 507 R; 560/13

[56] References Cited

U.S. PATENT DOCUMENTS 1,218,655   3/1917   Heymann et al. ................... 260/506

FOREIGN PATENT DOCUMENTS 9472 of 1914 United Kingdom ..................... 260/506

OTHER PUBLICATIONS

Willis, et al., Biochem. J., 47, 158 (1950).

Primary Examiner—Nicky Chan
Attorney, Agent, or Firm—Claude J. Caroli

[57] ABSTRACT

Ureylenebis(anionic substituted phenylene carbonyl)imino naphthalene sulfonic acids and naphthalene carboxylic acids and their salts, which are useful as inhibitors of the complement system of warm-blooded animals. Naphthyl sulfobenzoamido salts, which are new intermediates for the preparation of the active ureylenes, and the process for their preparation.

8 Claims, No Drawings

UREYLENEBIS(ANIONIC SUBSTITUTED PHENYLENE CARBONYL)IMINO NAPHTHALENE SULFONIC ACIDS AND NAPHTHALENE CARBOXYLIC ACIDS AND THEIR SALTS

This is a division of application Ser. No. 778,398 filed Mar. 17, 1977 now U.S. Pat. No. 4,129,590.

DESCRIPTION OF THE INVENTION

This invention is concerned with naphthalene sulfonic acid and naphthalene carboxylic acid ureylenes and their pharmaceutically acceptable salts, having complement inhibiting activity, which are new compounds of the general formula (I):

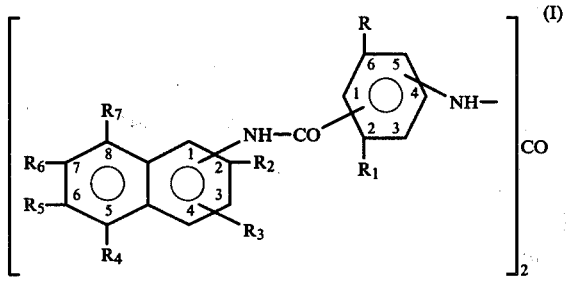

wherein R is selected from the group consisting of $SO_3X$ and $COOY$, wherein X is selected from the group consisting of alkali metal and Y is selected from the group consisting of hydrogen, alkali metal and $C_1$-$C_6$ alkyl; $R_1$, $R_4$, $R_5$, and $R_6$ are selected from the group consisting of hydrogen and $SO_3X$, wherein X is as previously defined; $R_2$ is selected from the group consisting of hydrogen and acetamido; with the proviso that there is no $R_1$ or $R_2$ substituent when the bridgehead carbonylimino is attached at the carbon 2-position of the respective ring; $R_3$ is selected from the group consisting of hydrogen, $SO_3X$ and $COOY$, wherein X and Y are as previously defined; $R_7$ is selected from the group consisting of hydrogen, hydroxy and $SO_3X$, wherein X is as previously defined; and the pharmaceutically acceptable salts thereof.

A preferred embodiment consists of those compounds wherein R, $R_1$, $R_2$, $R_3$, $R_4$, $R_5$, and $R_6$ are as previously defined; and $R_7$ is selected from the group consisting of $SO_3X$, wherein X is as previously defined.

A second preferred embodiment consists of those compounds wherein R, $R_1$, $R_2$, $R_3$, $R_4$, $R_5$ and $R_6$ are as previously defined; and $R_7$ is selected from the group consisting of hydroxy and hydrogen.

A third preferred embodiment consists of those compounds wherein $R_1$, $R_2$, $R_3$, $R_4$, $R_5$, $R_6$ and $R_7$ are as previously defined; and R is selected from the group consisting of $SO_3X$, wherein X is as previously defined.

A fourth preferred embodiment consists of those compounds wherein $R_1$, $R_2$, $R_3$, $R_4$, $R_5$, $R_6$ and $R_7$ are as previously defined; and R is selected from the group consisting of $COOY$, wherein Y is as previously defined.

A most preferred embodiment of the third preferred embodiment consists of those compounds wherein R, $R_1$, $R_3$, $R_4$, $R_5$, $R_6$ and $R_7$ are as previously defined; and $R_2$ is hydrogen.

A further preferred embodiment of the above most preferred embodiment consists of those compounds wherein R, $R_1$, $R_2$, $R_3$, $R_4$, $R_5$ and $R_6$ are as previously defined; and $R_7$ is selected from the group consisting of hydrogen and hydroxy.

A second further preferred embodiment of the above most preferred embodiment consists of those compounds wherein R, $R_1$, $R_2$, $R_3$, $R_4$, $R_5$ and $R_6$ are as previously defined; and $R_7$ is selected from the group consisting of $SO_3X$, wherein X is as previously defined.

A most preferred embodiment of fourth preferred embodiment consists of those compounds wherein R, $R_1$, $R_3$, $R_4$, $R_5$, $R_6$ and $R_7$ are as previously defined; and $R_2$ is hydroxy.

A further preferred embodiment of the above most preferred embodiment consists of those compounds wherein R, $R_1$, $R_2$, $R_3$, $R_4$, $R_5$ and $R_6$ are as previously defined; and $R_7$ is selected from the group consisting of hydrogen and hydroxy.

A second further preferred embodiment of the above most preferred embodiment consists of those compounds wherein R, $R_1$, $R_2$, $R_3$, $R_4$, $R_5$ are as previously defined; and $R_7$ is selected from the group consisting of $SO_3X$, wherein X is as previously defined.

This invention is also concerned with compounds of the formula (II):

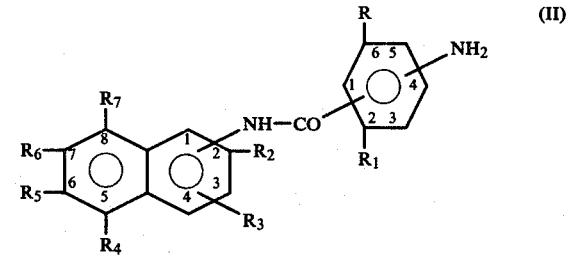

wherein R is selected from the group consisting of $SO_3X$ and $COOY$, wherein X is selected from the group consisting of hydrogen and alkali metal and Y is selected from the group consisting of hydrogen, alkali metal and $C_1$-$C_6$ alkyl; $R_1$, $R_4$, $R_5$ and $R_6$ are selected from the group consisting of hydrogen and $SO_3X$, wherein X is as previously defined; $R_2$ is selected from the group consisting of hydrogen and acetamido; with the proviso that there is no $R_1$ or $R_2$ substituent when the bridge-head carbonylimino is attached at the carbon 2-position of the respective ring; $R_3$ is selected from the group consisting of hydrogen, $SO_3X$ and $COOY$, wherein X and Y are as previously defined; and $R_7$ is selected from the group consisting of hydrogen, hydroxy and $SO_3X$, wherein X is as previously defined.

A preferred embodiment consists of those compounds wherein R, $R_1$, $R_2$, $R_3$, $R_4$, $R_5$ and $R_6$ are as previously defined; and $R_7$ is selected from the group consisting of $SO_3X$, wherein X is as previously defined.

A second preferred embodiment consists of those compounds wherein R, $R_1$, $R_2$, $R_3$, $R_4$, $R_5$ and $R_6$ are as previously defined; and $R_7$ is selected from the group consisting of hydroxy and hydrogen.

A third preferred embodiment consists of those compounds, wherein $R_1$, $R_2$, $R_3$, $R_4$, $R_5$, $R_6$ and $R_7$ are as previously defined; and R is selected from the group consisting of $SO_3X$, wherein X is as previously defined.

A fourth preferred embodiment consists of those compounds wherein $R_1$, $R_2$, $R_3$, $R_4$, $R_5$, $R_6$ and $R_7$ are as previously defined; and R is selected from the group consisting of COOY, wherein Y is as previously defined.

A most preferred embodiment of the third preferred embodiment consists of those compounds wherein R, $R_1$, $R_3$, $R_4$, $R_5$, $R_6$ and $R_7$ are as previously defined; and $R_2$ is hydrogen.

A further preferred embodiment of the above most preferred embodiment consists of those compounds wherein R, $R_1$, $R_2$, $R_3$, $R_4$, $R_5$ and $R_6$ are as previously defined; and $R_7$ is selected from the group consisting of hydrogen and hydroxy.

A second further preferred embodiment of the above most preferred embodiment consists of those compounds wherein R, $R_1$, $R_2$, $R_3$, $R_4$, $R_5$ and $R_6$ are as previously defined; and $R_7$ is selected from the group consisting of $SO_3X$, wherein X is as previously defined.

A most preferred embodiment of fourth preferred embodiment consists of those compounds wherein R, $R_1$, $R_3$, $R_4$, $R_5$, $R_6$ and $R_7$ are as previously defined; and $R_2$ is hydrogen.

A further preferred embodiment of the above most preferred embodiment consists of those compounds wherein R, $R_1$, $R_2$, $R_3$, $R_4$, $R_5$ and $R_6$ are as previously defined; and $R_7$ is selected from the group consisting of hydrogen and hydroxy.

A second further preferred embodiment of the above most preferred embodiment consists of those compounds wherein R, $R_1$, $R_2$, $R_3$, $R_4$, $R_5$ are as previously defined; and $R_7$ is selected from the group consisting of $SO_3X$, wherein X is as previously defined.

These compounds are useful as intermediates for the preparation of the complement inhibiting compounds described above. The compounds of the present invention may be prepared by the following method outlined in Flow Chart A.

Flow Chart A

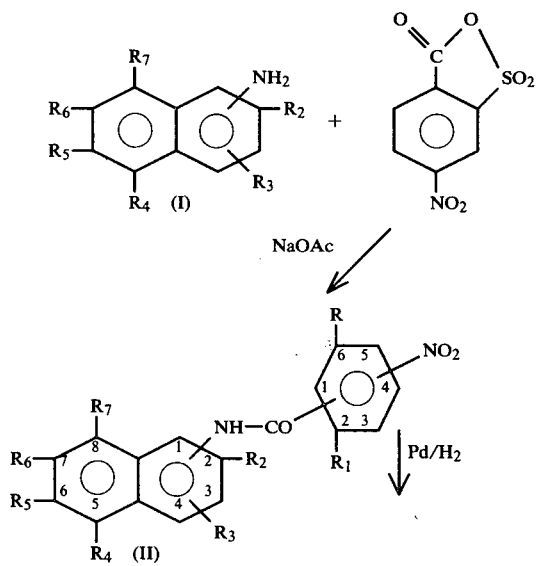

-continued
Flow Chart A

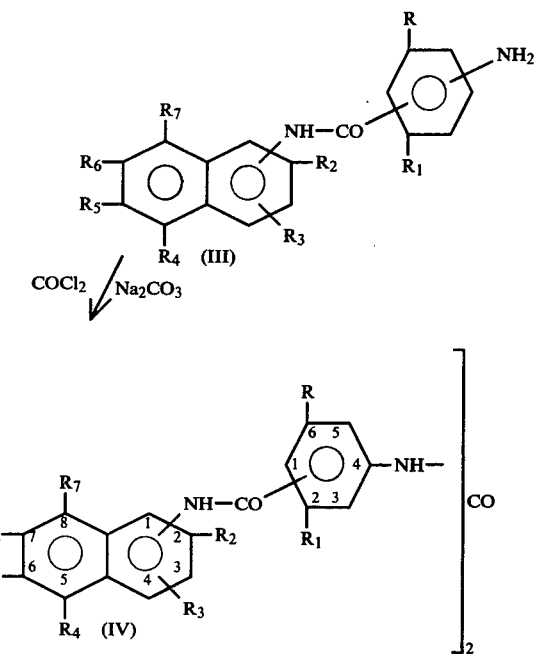

wherein R, $R_1$, $R_2$, $R_3$, $R_4$, $R_5$, $R_6$ and $R_7$ are as previously defined.

The novel intermediate amine compounds (III) of the invention are prepared by reacting the appropriate naphthylamine with a 15–20% excess of 4-nitro-2-sulfobenzoic anhydride in aqueous media with sodium acetate as a buffer at 0°–5° C. for approximately 10 minutes. Acidification of the mixture to approximately pH 1.0 followed by dilution with ethyl alcohol to approximately 80% aqueous ethyl alcohol results in precipitation of the nitroamide (II). Hydrogenation of the nitroamide using 10% palladium-carbon catalyst provides the intermediate amine (III).

The novel ureylene compounds (IV) of the invention, which are active complement inhibitors, are then provided by treatment of the amine (III) with phosgene in aqueous medium containing sodium carbonate.

A method of preparing the nitroamide, 8-(p-nitro-sulfobenzamino)-1,3,6-naphthalenetrisulfonic acid trisodium salt (IIa), as described in Flow Chart B, involves the reaction of 8-amino-1,3,6-naphthalenetrisulfonic acid trisodium salt (Ia) and p-nitrosulfobenzoic anhydride in base. The subsequent acidification and extraction of the aqueous solution with diethyl ether, followed by concentration and crystallization of the nitroamide (IIa) from the aqueous medium. The nitroamide is then hydrogenated and the amine (IIIa) is phosgenated to yield the product 8,8'-{ureylenebis[(2-sulfo-4,1-phenylenecarbonyl)imino]}di-1,3,6-naphthalenetrisulfonic acid hexasodium salt (IVa).

Flow Chart B

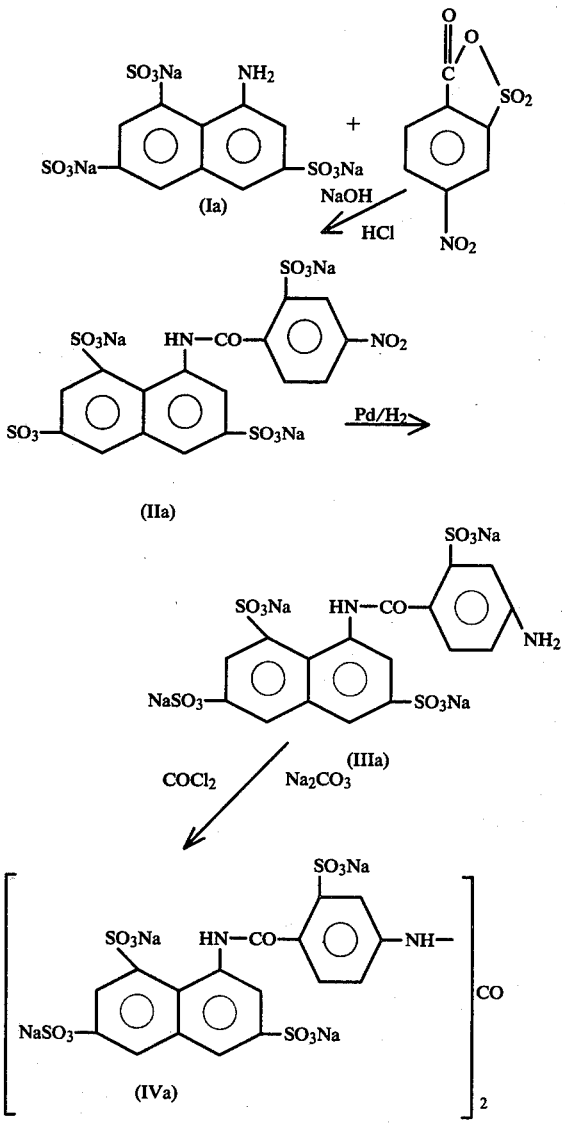

Alternatively, the reaction of 8-amino-1,3,6-naphthalenetrisulfonic acid trisodium salt and 8-amino-1,3,5-naphthalenetrisulfonic acid trisodium salt, respectively, with 5-nitroisophthaloyl chloride and 3-carbomethoxy-5-nitrobenzoyl chloride, respectively, in aqueous medium with sodium acetate as buffer, results in the recovery of the nitroamides 5-nitro-N-3,6,8-trisulfo-1-naphthylisophthalamic acid trisodium salt and 5-nitro-N-4,6,8-trisulfo-1-naphthylisophthalamic acid methyl ester trisodium salt, respectively, by crystallization from ethyl alcohol. Hydrogenation of the respective nitroamide provides the corresponding amine (III) which in turn is phosgenated to yield the respective novel ureide compound (IV).

The term "complement" refers to a complex group of proteins in body fluids that, working together with antibodies or other factors, play an important role as mediators of immune, allergic, immunochemical and/or immunopathological reactions. The reactions in which complement participates take place in blood serum or in other body fluids, and hence are considered to be humoral reactions.

With regard to human blood, there are at present more than 11 proteins in the complement system. These complement proteins are designated by the letter C and by number: C1, C2, C3 and so on up to C9. The complement protein C1 is actually an assembly of subunits designated C1q, C1r and C1s. The numbers assigned to the complement proteins reflect the sequence in which they become active, with the exception of complement protein C4, which reacts after C1 and before C2. The numerical assignments for the proteins in the complement system were made before the reaction sequence was fully understood. A more detailed discussion of the complement system and its role in body processes can be found in, for example, Bull. World Health Org., 39, 935–938 (1968); Ann. Rev. Medicine, 19, 1–25 (1968); The John Hopkins Med. J., 128, 57–74 (1971); Harvey Lectures, 66, 75–104 (1972); The New England Journal of Medicine, 287, 452–454; 489–495; 545–549; 592–596; 642–646 (1972); Scientific American, 229, (No. 5), 54–66 1 (1973); Federation Proceedings, 32, 134–137 (1973); Medical World News, Oct. 11, 1974, pp. 53–58; 64–66; J. Allergy Clin. Immunol., 53, 298–302 (1974); Cold Spring Harbor Conf. Cell Proliferation 2/Proteases Biol. Control/229–241 (1975); Annals of Internal Medicine, 84, 580–593 (1976); "Complement: Mechanisms and Functions", Prentice-Hall, Englewood Cliffs, N.J. (1976).

The complement system can be considered to consist of three sub-systems: (1) a recognition unit (C1q) which enables it to combine with antibody molecules that have detected to foreign invader; (2) an activation unit (C1r, C1s, C2, C4, C3) which prepares a site on the neighboring membrane; and (3) and attack unit (C5, C6, C7, C8 and C9) which creates a "hole" in the membrane. The membrane attack unit is non-specific; it destroys invaders only because it is generated in their neighborhood. In order to minimize damage to the host's own cells, its activity must be limited in time. This limitation is accomplished partly by the spontaneous decay of activated complement and partly by interference by inhibitors and destructive enzymes. The control of complement, however, is not perfect, and there are times when damage is done to the host's cells. Immunity is therefore a double-edged sword.

Activation of the complement system also accelerates blood clotting. The action comes about by way of the complement-mediated release of a clotting factor from platelets. The biologically active complement fragments and complexes can become involved in reactions that damage the host's cells, and these pathogenic reactions can result in the development of immune-complex diseases. For example, in some forms of nephritis, complement damages the basal membrane of the kidney, resulting in the escape of protein from the blood into the urine. The disease disseminated lupus erythematosus belongs in this category; its symptoms include nephritis, visceral lesions and skin eruptions. The treatment of diphtheria or tetanus with the injection of large amounts of antitoxin sometimes results in serum sickness, an immune-complex disease. Rheumatoid arthritis also involves immune complexes. Like disseminated lupus erythematosus, it is an autoimmune disease in which the disease symptoms are caused by pathological effects of the immune system in the host's tissues. In summary, the complement system has been shown to be involved with inflammation, coagulation, fibrinolysis, antibody-antigen reactions and other metabolic processes.

In the presence of antibody-antigen complexes the complement proteins are involved in a series of reactions which may lead to irreversible membrane damage if they occur in the vicinity of biological membranes. Thus, while complement constitutes a part of the body's defense mechanism against infection it also results in inflammation and tissue damage in the immunopathological process. The nature of certain of the complement proteins, suggestions regarding the mode of complement binding to biological membranes and the manner in which complement effects membrane damage are discussed in Annual Review in Biochemistry, 38, 389 (1969).

A variety of substances have been disclosed as inhibiting the complement system, i.e., as complement inhibitors. For example, the compounds 3,3'-ureylenebis-[6-(2-amino-8-hydroxy-6-sulfo-1-naphthylazo)]benzenesulfonic acid, tetrasodium salt (chlorazol fast pink), heparin and a sulphated dextran have been reported to have an anticomplementary effect, British Journal of Experimental Pathology, 33, 327–339 (1952). The compound 8-(3-benzamido-4-methylbenzamido)naphthalene-1,3,5-trisulfonic acid (Suramin) is described as a competitive inhibitor of the complement system, Clin. Exp. Immunol., 10, 127–138 (1972). German Pat. No. 2,254,893 or South African Pat. No. 727,923 discloses certain 1-(diphenylmethyl)-4-(3-phenylallyl)piperazines useful as complement inhibitors. Other chemical compounds having complement inhibiting activity are disclosed in, for example, Journal of Medicinal Chemistry, 12, 415–419; 902–905; 1049–1052; 1053–1056 (1969); Canadian Journal of Biochemistry, 47, 547–552 (1969); The Journal of Immunology, 93, 629–640 (1964); The Journal of Immunology, 104, 279–288 (1970); The Journal of Immunology, 106, 241–245 (1971); and The Journal of Immunology, 111, 1061–1066 (1973).

It has been reported that the known complement inhibitors epsilon-aminocaproic acid, Suramin and tranexamic acid all have been used with success in the treatment of hereditary angioneurotic edema, a disease state resulting from an inherited deficiency or lack of function of the serum inhibitor of the activated first component of complement (C1 inhibitor), The New England Journal of Medicine, 286, 808–812 (1972).

The compounds of the present invention may be administered internally, e.g., orally, intra-articularly or parenterally, e.g., intra-articular, to a warm-blooded animal to inhibit complement in the body fluid of the animal, such inhibition being useful in the amelioration or prevention of those reactions dependent upon the function of complement, such as inflammatory process and cell membrane damage induced by antigen-antibody complexes. A range of doses may be employed depending on the mode of administration, the condition being treated and the particular compound being used. For example, for intravenous or subcutaneous use from about 5 to about 50 mg/kg/day, or every six hours for more rapidly excreted salts, may be used. For intra-articular use for large joints such as the knee, from about 2 to about 20 mg/joint per week may be used, with proportionally smaller doses for smaller joints. The dosage range is to be adjusted to provide optimum therapeutic response in the warm-blooded animal being treated. In general, the amount of compound administered can vary over a wide range to provide from about 5 mg/kg to about 100 mg/kg of body weight of animal per day. The usual daily dosage for a 70 kg subject may vary from about 350 mg to about 3.5 g. Unit doses of the acid or salt can contain from about 0.5 mg to about 500 mg.

While in general the sodium salts of the acids of the invention are suitable for parenteral use, other salts may also be prepared, such as those of primary amines, e.g., ethylamine; secondary amines, e.g., diethylamine or diethanol amine; tertiary amines, e.g., pyridine or triethylamine or 2-dimethylaminomethyl-dibenzofuran; aliphatic diamines, e.g., decamethylenediamine; and aromatic diamines, can be prepared. Some of these are soluble in water, others are soluble in saline solution, and still others are insoluble and can be used for purposes of preparing suspensions for injection. Furthermore as well as the sodium salt, those of the alkali metals, such as potassium and lithium; of ammonia; and of the alkaline earth metals, such as calcium or magnesium, may be employed. It will be apparent, therefore, that these salts embrace, in general derivatives of salt-forming cations.

In terapeutic use, the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety of forms depending on the form of preparation desired for administration, i.e., oral or parenteral. The compounds can be used in compositions such as tablets. Here, the principal active ingredient is mixed with conventional tabletting ingredients such as corn starch, lactose, sucrose, sorbitol, talc, stearic acid, magnesium stearate, dicalcium phosphate, gums, or similar materials as nontoxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and on outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate non-toxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term dosage form, as described herein, refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification for the novel dosage forms of this invention are indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The complement inhibiting activity of the compounds of this invention has been demonstrated by one or more of the following identified tests: (i) Test, Code 026 (C1 inhibitor)—This test measures the ability of activated human C1 to destroy fluid phase human C2 in the presence of C4 and appropriate dilutions of the test compound. An active inhibitor protects C2 from C1 and C4; (ii) Test, Code 035 (C3–C9 inhibitor)—This test determines the ability of the late components of human complement (C3–C9) to lyse EAC 142 in the presence of appropriate dilutions of the test compound. An active inhibitor protects EAC 142 from lysis by human C3–C9; (iii) Test, Code 036 (C-Shunt inhibitor)—In this test human erythrocytes rendered fragile are lysed in autologous serum via the shunt pathway activated by cobra venom factor in the presence of appropriate dilutions of the test compound. Inhibition of the shunt pathway results in failure of lysis; (iv) Forssman Vasculitis Test—Here, the well known complement dependent lesion, Forssman vasculitis, is produced in guinea pigs by intradermal injection of rabbit anti-Forssman antiserum. The lesion is measured in terms of diameter, edema and hemorrhage and the extent to which a combined index of these is inhibited by prior intraperitoneal injection of the test compound at 200 mg/kg is then reported, unless otherwise stated; (v) Forssman Shock Test—Lethal shock is produced in guinea pigs by an i.v. injection of anti-Forssman antiserum and the harmonic mean death time of treated guinea pigs is compared with that of simultaneous controls; (vi) Complement Level Reduction Test—In this test, the above dosed guinea pigs, or others, are bled for serum and the complement level is determined in undiluted serum by the capillary tube method of U.S. Pat. No. 3,876,376 and compared to undosed control guinea pigs; and (vii) Cap 50 Test—Here, appropriate amounts of the test compound are added to a pool of guinea pig serum in vitro, after which the undiluted serum capillary tube assay referred to above is run. The concentration of compound inhibiting 50% is reported.

With reference to Table I, guinea pigs weighing about 300 g were dosed intravenously (i.v.) or intraperitoneally (i.p.) with 200 mg/kg of the test compound dissolved in saline and adjusted to pH 7–8. One hour after dosing, the guinea pigs were decapitated, blood was collected and the serum separated. The serum was tested for whole complement using the capillary tube assay. Percent inhibition was calculated by comparison with simultaneous controls. The results appear in Table I together with results of tests, Code 026, 035, 036, Cap 50, percent inhibition and Forssman shock. Table I shows that the compounds of the invention possess highly significant in vitro and in vivo, complement inhibiting activity in warm-blooded animals.

TABLE I

| | Biological Activities | | | | In Vivo Activity (Guinea Pig) % Inhibition | | | | | |
|---|---|---|---|---|---|---|---|---|---|---|
| | Cl 026* | C-Late 035* | Shunt Inhibition 036* | | Intraperitoneal Time (mins.) | | | Intravenous Time (mins.) | | |
| Compound | Wells | Wells | Wells | Cap 50* | 30 | 60 | 120 | 2 | 30 | 120 |
| 8,8'-[Ureylenebis(4,1-phenylenecarbonylimino)]di-1,3,6-naphthalenetrisulfonic acid hexasodium salt | +4** +4 | +1 N | +3 N | 290 | −18 | −21 | −33 | −71 | −28 | −16 |
| 8,8'-{Ureylenebis{[(2-sulfo-p-phenylene)carbonyl]imino}}-1,3,6-naphthalenetrisulfonic acid octasodium salt | +7 +8 +8 | +1 N +1 | +3 N +4 | 130 | +4 | +17 | −8 | −85 | −53 | −24 |
| 5,5'-[Ureylenebis(2-sulfo-4,1-phenylenecarbonylimino)]bis[6-acetamido-1,3-naphthalenedisulfonic acid] hexasodium salt | +8 | N | +1 | 305 | −19 | +8 | +4 | | | |
| 4,4'-{Ureylenebis[(2-sulfo-4,1-phenylenecarbonyl)imino]}bis[5-hydroxy-2,7-naphthalenedisulfonic acid]hexasodium salt | +9 +6 +6 | +1 +1 +2 | +3 +2 +4 | 194 80 | −35 | −41 | −74 | −98 | −81 | −63 |
| 8,8'-{Ureylenebis[(2-sulfo-4,1-phenylenecarbonyl)imino]}di-1,3,5-naphthalenetrisulfonic acid octasodium salt | +8 +7 +8 | +1 +1 +1 | +1 +3 +3 | 104 | −32 | −31 | −51 | −89 | −45 | −29 |
| 3,3'-{Ureylenebis[(2-sulfo-4,1-phenylene)carbonylimino]}di-2-naphthoic acid tetrasodium salt | N | +3 | N | >500 | | | | | | |
| 4,4'{Ureylenebis[(2-sulfo-4,1-phenylenecarbonyl)imino]}di-2,7-naphthalenedisulfonic acid hexasodium salt | +4 +5 | N +1 | N N | >500 | | | | | | |
| 5,5'-{Ureylenebis[(2-sulfo-4,1-phenylenecarbonyl)imino]}bis[4-hydroxy-2-naphthalenesulfonic acid] tetra- | +2 +2 | N +1 | +1 N | 102 | −26 | 0 | −58 | | | |

TABLE I-continued

| | Biological Activities | | | | In Vivo Activity (Guinea Plg) % Inhibition | | | | | |
|---|---|---|---|---|---|---|---|---|---|---|
| | Cl 026* | C-Late 035* | Shunt Inhibition 036* | | Intraperitoneal Time (mins.) | | | Intravenous Time (mins.) | | |
| Compound | Wells | Wells | Wells | Cap 50* | 30 | 60 | 120 | 2 | 30 | 120 |
| sodium salt | | | | | | | | | | |
| 4,4'-Ureylenebis[(2-sulfo-4,1-phenylenecarbonyl)imino]bis[5-hydroxy-1,7-naphthalenedisulfonic acid] hexasodium salt | +7 | N | +5 | <100 | +1 | −3 | −24 | | | |
| 8,8'[Ureylenebis(2-sulfo-4,1-phenylenecarbonylimino)]di-1,6-naphthalenedisulfonic acid hexasodium salt | +5 | +1 | +1 | 297 | −10 | −18 | −31 | | | |
| 4,4'-{Ureylenebis[(2-sulfo-4,1-phenylenecarbonyl)imino]}di-1,6-naphthalenedisulfonic acid hexasodium salt | +5 | N | N | 277 | −3 | −4 | +6 | | | |
| 4,4'-{Ureylenebis[(2-sulfo-4,1-phenylenecarbonyl)imino]}di-2,6-naphthalenedisulfonic acid hexasodium salt | +5 | N | N | 170 | −3 | −4 | −11 | | | |
| 4,4'-{Ureylenebis[(2-sulfo-4,1-phenylenecarbonyl)imino]}di-1,5-naphthalenedisulfonic acid trisodium salt | +7 | N | +1 | | −10 | +6 | −6 | | | |
| 5,5'-Ureylenebis[N-(3,6,8-trisulfo-1-naphthyl)]isophthalamic acid octasodium salt | +10 | N | +2 | 146 | −37 | −42 | −48 | −92 | −44 | −39 |
| 5,5'-Ureylenebis[N-(4,6,8-trisulfo-1-naphthyl)isophthalamic acid]dimethyl ester hexasodium salt | +4 | +1 | +1 | 249 | −14 | −17 | −25 | | | |
| 5,5'-Ureylenebis[N-(4,6,8-trisulfo-1-naphthyl)isophthalamic acid]octasodium salt | +5 | +1 | +2 | <100 | −40 | −49 | −71 | | | |
| 3,3'-Ureylenebis{5-[(8-hydroxy-4,6-disulfo-1-naphthyl)aminocarbonyl]-benzoic acid tetrasodium salt | +4 +4 | +2 +4 | +2 | 129 | | | | | | |
| 4,4'-{Ureylenebis[(6-methyl-3,1-phenylenecarbonyl)imino]}bis[5-hydroxy-1,7-naphthalenedisulfonic acid],tetrasodium salt | +4 +8 | +1 +3 | +2 | | | | | | | |
| 8,8'-[Carbonylbis{(imino-6-sulfo-3,1-phenylene)carbonylimino]}bis-1,3,6-naphtholenetrisulfonic acid octosodium salt | +7 +4 | +1 +4 | +1 | <100 | −23 | −58 | −71 | | | |
| 8,8'-{Carbonylbis[(imino-6-sulfo-3,1-phenylene)carbonylimino]}bis-1,3,6-naphthalenetrisulfonic acid octosodium salt | +7 | | | 48 | | | −71 | | | |
| 3,3-(Carbonyldiimino)bis{5-[(8-hydroxy-3,6-disulfo-1-naphthalenyl)aminocarbonyl]}benzoic acid tetrasodium salt | +6 | | | 56 | | | −69 | | | |
| 3,3'-Ureylenebis{5-[(8-hydroxy-4,6-disulfo-1-naphthyl)aminocarbonyl]}-benzoic acid tetrasodium salt | +4 | | | 129 | | | −94 | | | |

N = Negative
*Code designation for tests employed as referred to herein.
**Activity in wells, a serial dilution assay. Higher well number indicates higher activity. The serial dilutions are two-fold.

SPECIFIC DISCLOSURE

EXAMPLE 1

8-(p-Aminobenzamido)-1,3,6-naphthalenetrisulfonic acid trisodium salt

To a solution of 27.0 g of 8-amino-1,3,6-naphthalenetrisulfonic acid trisodium salt in 100 ml of water and 60 ml of N sodium hydroxide is added 22.5 g of p-nitrobenzoyl chloride and 30 ml of diethyl ether. The reaction mixture is shaken in a separatory funnel for about 15 minutes, and another 60 ml portion of base is added. After shaking for 15 minutes the procedure is repeated with two additional 60 ml portions of base. The reaction mixture is acidified with 7.5 ml of concentrated hydrochloric acid and diluted with 250 ml of water, then extracted 9 times with 300 ml portions of ether. The aqueous phase is neutralized with 5 N sodium hydroxide and allowed to stand overnight at room temperature, then is filtered through diatomaceous earth. The filtrate is concentrated to a low volume in vacuo at 55°–60° C. The crystalline solid formed is collected by filtration, washed and slurried with absolute ethyl alcohol to yield 28.6 g of 8-(p-nitrobenzamido)-1,3,6-naphthalenetrisulfonic acid trisodium salt.

A mixture of 25.0 g of the above product, 100 ml of water and 2.5 g of 10% palladium catalyst on carbon is hydrogenated at room temperature for 2 hours and 40 minutes at an average pressure of 37 pounds, then is filtered through diatomaceous earth and washed with water. The filtrate is concentrated to a small volume in vacuo at 55°–60° C. resulting in the formation of off-white crystals. The material is diluted with about 300 ml of absolute ethyl alcohol, triturated, filtered and washed with absolute ethanol and dried at 120° C. overnight to give 21.8 g of 8-(p-aminobenzamido)-1,3,6-naphthalenetrisulfonic acid trisodium salt as yellow crystals.

EXAMPLE 2

8,8'-[Ureylenebis(4,1-phenylenecarbonylimino)]di-1,3,6-naphthalenetrisulfonic acid hexasodium salt Phosgene is bubbled into a solution of 10.0 g of the product of Example 1 and 18.6 g of anhydrous sodium carbonate in 250 ml of water until the solution is acidic. An additional 18.6 g of the sodium carbonate is added and phosgene is bubbled through for an additional hour. The reaction mixture is brought to pH 8 by the addition of 75 ml of 5 N sodium hydroxide, then is neutralized with a few drops of 10% hydrochloric acid. The solution is concentrated in vacuo at 50°–55° C. to about 200 ml and is cooled to room temperature. The precipitate formed is collected by filtration and washed with 200 ml of 90% ethyl alcohol followed by 250 ml of absolute ethyl alcohol. The product is oven dried at 120° C. overnight, then is slurried with 200 ml of boiling absolute methyl alcohol and cooled to room temperature. The product of the example is collected, washed with cold methyl alcohol and oven dried for 48 hours at 120° C. to give a colorless powder.

EXAMPLE 3

8-(4-Amino-2-sulfobenzamido)-1,3,6-naphthalenetrisulfonic acid tetrasodium salt

A solution of 100 g of 5-nitro-o-toluenesulfonic acid in 600 ml of water plus 80 ml of 5 N sodium hydroxide is heated to 90° C. in a 2 liter Erlenmeyer flask, then 240 g of potassium permanganate is added portionwise to maintain refluxing over 75 minutes. The mixture is filtered and the residue is washed with water. The combined filtrate and washings are concentrated in vacuo and allowed to crystallize to give 86.2 g of crude 4-nitro-2-sulfobenzoic acid sodium potassium salt. Recrystallization from water gives 71.3 g of purified product.

The total product above is dissolved in 250 ml of water plus 35 ml of concentrated hydrochloric acid by warming on a steam-bath. The solution is then diluted with 300 ml of ethyl alcohol and allowed to crystallize at room temperature. The mixture is allowed to stand 48 hours in a chill room, then is filtered. The precipitate is washed with cold 50% aqueous ethyl alcohol, then with ethanol and ether. The material is recrystallized from 200 ml of water and is dried at 110° C. to give 52.0 of 4-nitro-2-sulfobenzoic acid, 2-sodium salt.

A 50.0 g portion of the preceding compound and 500 g of thionyl chloride are stirred and refluxed for 19 hours. The mixture is evaporated in vacuo, and the residue is warmed with 300 ml of toluene and filtered. The filtrate is concentrated in vacuo, and the product is crystallized twice from toluene to give 30.4 g of 4-nitro-2-sulfobenzoic acid anhydride.

To an ice-bath cooled solution (5° C.) of 8-amino-1,3,6-naphthalenetrisulfonic acid trisodium salt and 6.7 g of sodium acetate trihydrate in 100 ml of water is added 8.8 g of 4-nitro-2-sulfobenzoic acid anhydride. The mixture is stirred vigorously for 10 minutes and is filtered. The filtrate is cooled in an ice bath and diluted with 500 ml of cold ethyl alcohol. The mixture is filtered and the product is washed with ethyl alcohol and ether and then is dried. The product is dissolved in 50 ml of warm water and is stirred for 10 minutes after the addition of one ml of acetone. The mixture is treated with activated charcoal, filtered through diatomaceous earth and is washed with 20 ml of water. The filtrate is cooled in an ice bath and acidified with 1.5 ml of concentrated hydrochloric acid. The solution is diluted with 500 ml of cold ethyl alcohol, and the precipitated material is filtered, washed with ethanol followed by ether and dried. The above purification process is repeated without acidification. The product obtained is dried overnight at 110° C. to give 18.5 g of 8-(4-nitro-2-sulfobenzamido)-1,3,6-naphthalenetrisulfonic acid tetrasodium salt.

A 17.5 g portion of the preceding product and 1.5 g of palladium catalyst on carbon in 150 ml of water is hydrogenated for one hour at room temperature then is filtered through diatomaceous earth. The filtrate is concentrated and the product is precipitated by the addition of absolute ethanol. The product is collected and dried overnight in an abderhalden apparatus at 110° C. to give 14.5 g of 8-(4-amino-2-sulfobenzmido)-1,3,6-naphthalenetrisulfonic acid tetrasodium salt as a powder.

EXAMPLE 4

8,8'-{Ureylenebis{[(2-sulfo-4,1-phenylene)carbonyl-]imino}}-1,3,6-naphthalenetrisulfonic acid octasodium salt Phosgene gas is passed through a solution of 5.5 g of the product of Example 3 in 40 ml of water and 3.8 ml of pyridine until the solution is acidic. The solution is back neutralized with 0.2 ml of pyridine, then is poured into 250 ml of absolute ethyl alcohol. A gum is formed which solidifies on standing. The gum is ground up and washed on a filter with ethyl alcohol and ether. The material is dissolved in 35 ml of water, is made basic (pH 8–9) with 5 N sodium hydroxide and is filtered through diatomaceous earth. The filtrate is poured into 350 ml of absolute ethyl alcohol and is reacidified with a few drops of acetic acid. The product formed is collected and dried by conventional means to give the product of the Example as a beige powder.

EXAMPLE 5

6-Acetamido-5-(4-amino-2-sulfobenzamido)-1,3-naphthalenedisulfonic acid trisodium salt To a solution of 27.6 g of p-nitroaniline in a mixture of 170 ml of acetic acid, 50 ml of concentrated hydrochloric acid, 100 ml of water and 200 ml of crushed ice, cooled in an ice-bath is added 13.8 g of sodium nitrite in 25 ml of water with stirring [solution (A)]. Stirring is continued during preparation of a solution of 65 g of (about 92.5%) 6-amino-1,3-naphthalenedisulfonic acid in 80 ml of 5 N sodium hydroxide and 100 ml of water [solution (B)]. A 57 g amount of sodium acetate trihydrate is added to solution (A) followed by the addition of solution (B). The mixture is heated on a steam bath (60° C.) until dissolved, then is filtered and allowed to crystallize at room temperature. The mixture is then cooled to 10° C. The product is collected and washed with 300 ml of 20% aqueous solution of sodium acetate trihydrate followed by ethyl alcohol and ether. The material is dried in vacuo to give 87.0 g of 6-amino-5-(pnitrophenylazo)-1,3-naphthalenedisulfonic acid disodium salt as a crystalline product.

To 300 ml of acetic anhydride cooled in an ice-bath is added portionwise 100 g of concentrated sulfuric acid, while keeping the temperature below 20° C. To this solution is added, portionwise and with stirring, 50 g of the preceding product keeping the temperature below 20° C. The mixture is stirred at room temperature for one hour, then is cooled to about 7° C. and is filtered. The product is washed on the filter with acetone, then is stirred with two successive 500 ml portions of acetone and is filtered again and dried on the filter to give 49.4 g of product. A 49.0 g portion of this material is dissolved in 300 ml of water and is neutralized to pH 6.7 with 20 g of sodium bicarbonate. The solution is then acidified to pH 5.5 with acetic acid and is filtered. The filtrate is evaporated in vacuo to about 250 ml, and is poured into 1800 ml of vigorously stirring absolute ethyl alcohol. The precipitate formed is collected by filtration and is washed with ethyl alcohol followed by ether. A 47.0 g quantity of material dried in vacuo is additionally dried overnight in the Abderhalden apparatus at 110° C. to give 46.5 g of 6-acetamido-5-(p-nitrophenylazo)-1,3-naphthalenedisulfonic acid disodium salt as a red-brown powder.

A 23.0 g portion of the above product and 1.5 g of palladium catalyst on carbon in 150 ml of water is hydrogenated in a Parr shaker at room temperature for 1.5 hours. The mixture is filtered through diatomaceous earth and the filtrate is concentrated to 80–100 ml. This solution is poured into 600 ml of ice-cold ethyl alcohol with vigorous stirring in a baffle flask. The mixture is stirred 3–4 minutes then filtered. The product is washed with ethyl alcohol and ether and is dried overnight at 65° C. in an Abderhalden apparatus to give 16.15 g of 6-acetamido-5-amino-1,3-naphthalenedisulfonic acid disodium salt as a powder.

To a solution of 12.76 g of the preceding compound and 6.25 g of sodium acetate trihydrate in 75 ml of water, cooled to 3° C. is added 8.25 g of 4-nitro-2-sulfobenzoic acid anhydride. The mixture is stirred 10 minutes, treated with activated charcoal and filtered through diatomaceous earth. The filtrate is concentrated to 50 ml, is cooled in an ice-bath, acidified with 2.5 ml of concentrated hydrochloric acid and poured with vigorous stirring into 500 ml of ice cold ethyl alcohol. The resulting gelatinous precipitate is collected by filtration and washed with ethyl alcohol. The product is stirred in ether, is filtered and is dried in vacuo to yield a powder. The product is further purified by extraction with methanol, filtering and evaporation. The material is dried overnight in an Abderhalden apparatus at 110° C. to yield 6.06 g of 6-acetamido-5-(4-nitro-2-sulfobenzamido)-1,3-naphthalenedisulfonic acid trisodium salt as a powder.

A 5.0 g portion of the above product and 1.0 g of palladium catalyst on carbon in 50 ml of water is hydrogenated for one hour during which time 2.2 pounds of hydrogen are absorbed. The mixture is filtered through diatomaceous earth to remove the catalyst and the filtrate is concentrated to give the product of the example.

EXAMPLE 6

5,5'-[Ureylenebis(2-sulfo-1,4-phenylenecarbonylimino)]bis[6-acetamido-1,3-naphthalenedisulfonic acid]hexasodium salt The product of Example 5 is diluted to approximately 35 ml with water, then 4.0 ml of pyridine is added and phosgene is passed through until the solution is just acidic. Additional pyridine is added to make the solution weakly basic, then it is poured with vigorous stirring into 350 ml of ethyl alcohol. The resulting mixture is filtered and the product is washed with ethyl alcohol and ether to yield an orange powder. The powder is dissolved in 15 ml of water and the solution is made basic with 1.5 ml of 5 N sodium hydroxide, then is quickly back neutralized with acetic acid. The solution is poured into 200 ml of absolute ethyl alcohol and heated on a steam bath to near boiling. The mixture is then cooled to room temperature and filtered. The product is washed with ethyl alcohol and ether and is dried overnight at 110° C. to give the product of the example as a powder.

EXAMPLE 7

4-(4-Amino-2-sulfobenzamido)-5-hydroxy-2,7-naphthalenedisulfonic acid trisodium salt A 14.36 g portion of 8-amino-1-naphthol-3,6-disulfonic acid monosodium salt is dissolved in 40 ml of N sodium hydroxide with slight warming. This solution is slowly added to ethyl alcohol with stirring forming an off-white solid which is filtered, washed with ethyl alcohol and ether and is dried in vacuo to yield 11.0 g of the disodium salt. A 7.26 g portion of the above product and 4.28 g of sodium acetate trihydrate is dissolved in 60 ml of water. The solution is cooled to 0° C. and 5.44 g of 4-nitro-2-sulfobenzoic acid anhydride is added all at once with stirring. Stirring is continued for 10 minutes and the solution is filtered. The filtrate is cooled in an ice bath, is acidified with 1.76 ml of concentrated hydrochloric acid then added to about 400 ml of ethyl alcohol. The total volume is brought to 800 ml by addition of more ethyl alcohol. The mixture is stirred for 15 minutes and is filtered. The precipitate is washed with ethyl alcohol followed by ethyl ether and is dried in vacuo at 78° C. to yield 7.3 g of 4-hydroxy-5-(4-nitro-2-sulfobenzamido)-2,7-naphthalenedisulfonic acid trisodium salt.

A 7.5 g portion of the preceding compound and 800 mg of 10% palladium catalyst on carbon in 125 ml of water is hydrogenated in a Parr shaker until no more hydrogen is absorbed. The mixture is filtered through diatomaceous earth and the filtrate is evaporated at 60° C. The residue obtained is dissolved in about 25 ml of ethyl alcohol and is added to 400 ml of ethyl alcohol. The mixture is stirred for ½ hour and filtered. The precipitate is washed with ethyl alcohol and ether, then is dried in vacuo overnight to yield 5.6 g of the product of the example.

EXAMPLE 8

4,4'-{Ureylenebis[(2-sulfo-4,1-phenylenecarbonyl)imino]}bis-[5-hydroxy-2,7-naphthalenedisulfonic acid]hexasodium salt Phosgene gas is passed through a solution of 4.7 g of the product of Example 7 and 1.71 g of anhydrous sodium carbonate in 30 ml of water at room temperature until the solution becomes acidic to Congo Red indicator paper. The reaction mixture is filtered and the pH is adjusted to 7.2 with sodium carbonate, and then evaporated. The residue is dissolved in a minimum amount of water and ethanol is added to precipitate 2.3 g of product as a solid.

EXAMPLE 9

8-(4-Amino-2-sulfobenzamido)-1,3,5-naphthalenetrisulfonic acid tetrasodium salt

To a warm solution of 23.8 g of 80.5% 8-amino-1,3,5-naphthalenetrisulfonic acid in 25 ml of water and 25 ml of 5 N sodium hydroxide are slowly added 125 ml of absolute ethyl alcohol with vigorous stirring. The mixture is cooled to room temperature, is filtered and washed with 50 ml of 80% aqueous ethyl alcohol, then ethyl alcohol and ether. The material is dried overnight at 110° C. to give 21.0 g of 8-amino-1,3,5-naphthalenetrisulfonic acid trisodium salt as a powder.

A 4.49 g portion of the material above and 2.14 g of sodium acetate trihydrate is dissolved in 30 ml of water. The solution is cooled to 0° C. in an ice bath and 2.72 g of 4-nitro-2-sulfobenzoic acid anhydride is added at one time. After a few minutes the ice bath is removed and the solution is stirred for a total of 20 minutes. The solution is filtered and the filtrate acidified with 0.88 ml of concentrated hydrochloric acid. The solution is evaporated and the residue is dissolved in 10 ml of water, then is added to 200 ml of ethyl alcohol and is stirred for ½ hour. The precipitate is collected by filtration and washed with ethyl alcohol and ether and is dried in vacuo. The dried material is dissolved in 10 ml of hot water, and 50 ml of absolute ethyl alcohol is added with stirring for ½ hour. An additional 20 ml of ethyl alcohol is added with stirring continued for 10 minutes. The precipitate is then collected by filtration, washed with ethyl alcohol and ether and dried in an Abderhalden apparatus at 110° C. overnight to yield 4.5 g of product. The product is recycled through the procedure described above using 1.07 g of sodium acetate trihydrate, 1.36 g of 4-nitro-2-sulfobenzoic acid anhydride and 0.44 ml of concentrated hydrochloric acid, respectively. After the material is dried in vacuo as previously described, the dried material is dissolved in 10 ml of hot water and 70 ml of ethyl alcohol is added slowly with stirring at room temperature for one hour. The precipitate is collected by filtration and is washed with 80% aqueous ethyl alcohol, ethyl alcohol and ether, then is dried as previously described to afford 4.5 g of 8-(p-nitro-2-sulfobenzamido)-1,3,5-naphthalenetrisulfonic acid tetrasodium salt as a solid.

A 3.9 g portion of the above compound and 400 mg of 10% palladium catalyst on carbon in 50 ml of water is hydrogenated, filtered and concentrated as described in Example 7. The residue obtained is dissolved in 10 ml of hot water and 100 ml of absolute ethyl alcohol is added. An oily precipitate is formed which is redissolved by addition of more ethyl alcohol. The solvent is then evaporated in vacuo to give 3.7 g of 8-(4-amino-2-sulfobenzamido)-1,3,5-naphthalenetrisulfonic acid tetrasodium salt.

EXAMPLE 10

8,8'-{Ureylenebis[(2-sulfo-4,1-phenylenecarbonyl)imino]}di-1,3,5-naphthalenetrisulfonic acid octasodium salt Phosgene is bubbled into a solution of 3.7 g of the product of Example 9 and 1.21 g of anhydrous sodium carbonate in 30 ml of water at room temperature until the mixture is acidic to Congo red indicator. The solution is neutralized with sodium carbonate and then is concentrated. The residue is dissolved in 10 ml of hot water and 100 ml of absolute ethyl alcohol is added with separation of an oil. The material is redissolved and reconcentrated. The residue is again dissolved in 10 ml of hot water and 80 ml of absolute ethyl alcohol is added with separation of an oil which does not dissolve on warming. The supernatant is decanted and ethyl alcohol is added to the oil which solidifies on being stirred. The solid is filtered, washed with ethyl alcohol and ether and dried. The dried material is dissolved in 10 ml of hot water, and 35 ml of ethyl alcohol is added with the separation of an oil. Water is added to effect solution, and the solution is cooled in an ice-box whence the oil is again separated. The mixture is heated to solution and 40 ml of absolute ethyl alcohol is added again with the separation of an oil. The supernatant while hot is decanted and the residue is triturated with ethyl alcohol to provide a solid which is stirred for ½ hour. The solid is collected by filtration, washed with ethyl alcohol and ether and dried in vacuo to yield 3.15 g of the product of the example as a yellow solid.

EXAMPLE 11

3-(4-Amino-2-sulfobenzamido)-2-naphthoic acid

A 3.74 g portion of 2-amino-3-naphthoic acid and 4.28 g of sodium acetate trihydrate in 30 ml of water is neutralized with 4 ml of 5 N sodium hydroxide. The solution is filtered and 30 ml of water is added to the filtrate. The solution is cooled to 0° C. and 5.44 g of 4-nitro-2-sulfobenzoic acid anhydride is added at one time to the stirred solution, then about 250 ml of water is added to insure solution and stirring is continued for 20 minutes. The solution is filtered, the filtrate is acidified with 1.76 ml of concentrated hydrochloric acid and heated to solubilize the formed precipitate. The solution is then cooled and allowed to stand. The solid is collected by filtration and is air dried to give 6.3 g of 3-(4-nitro-2-sulfobenzamido)-2-naphthoic acid sodium salt as a yellow solid.

To a 5.64 g portion of the above compound in 60 ml of water is added 12.85 ml of N sodium hydroxide. Additional water is added to achieve almost complete solution. The solution is filtered, 500 mg of 10% palladium catalyst on carbon is added and the mixture is hydrogenated in a Parr shaker until no more hydrogen is absorbed. The mixture is filtered through diatomaceous earth and the filter is washed with water. The filtrate and washes are combined and evaporated. The residue is dissolved in 40–50 ml of water and is acidified to pH 3. The precipitate formed is collected by filtration and is washed with water and acetone. The material is air-dried to yield 4.5 g of the product of the example.

EXAMPLE 12

3,3'-{Ureylenebis[(2-sulfo-4,1-phenylene)carbonylimino]}di-2-naphthoic acid tetrasodium salt A 3.817 g portion of the product of Example 11 in 30 ml of water is neutralized to pH 7.5–8 with N sodium hydroxide, then 1.99 g of anhydrous sodium carbonate is added and phosgene gas is passed in until the solution is acidic to Congo red indicator. The precipitate so formed is collected by filtration, and is washed with water, acetone and ethyl ether, then is dried in vacuo to yield 3.0 g of 3,3'-{ureylenebis[(2-sulfo-4,1-phenylene)-carbonylimino]}di-2-naphthoic acid disodium salt.

The material above is slurried in 15 ml of water and is treated with 5 N sodium hydroxide until solution is just achieved. The precipitate which then reappears is collected, and washed sparingly with water, then washed with ethyl alcohol and ether. The material is dried by conventional means to afford 1.0 g of a white solid as the product of the example.

EXAMPLE 13

4-(4-Amino-2-sulfobenzamido)-2,7-naphthalenedisulfonic acid trisodium salt

A 151.7 g portion of 1-amino-3,6-naphthalenedisulfonic acid is added with stirring to 200 ml of water containing 44 g of sodium hydroxide. This solution is treated with activated charcoal and filtered. To the filtrate is added ethyl alcohol with the formation of a precipitate which is allowed to stand. The solid is collected by filtration and set aside. More ethyl alcohol is added to the filtrate with the formation of additional product. This product is collected after standing and is combined with the material previously set aside. The combined product is dissolved in water, treated with activated charcoal and is recrystallized from ethyl alcohol. The product is collected by filtration, washed with absolute ethyl alcohol and is dried to give 1-amino-3,6-naphthalenedisulfonic acid disodium salt.

A 20.82 g portion of the preceding product and 8.2 g of sodium acetate is dissolved in 75 ml of water. The solution is cooled to about 2° C. in an ice bath and 14.4 g of 4-nitro-2-sulfobenzoic acid anhydride is added all at once. Approximately 15 minutes after the addition is complete, the ice-bath is removed and stirring is continued for an additional 45 minutes. The reaction mixture is then filtered and 150 ml of absolute ethanol is added resulting in formation of a precipitate which is collected by filtration and washed with absolute ethanol and ether. The material is dried by conventional means to give 20.70 g of 4-(4-nitro-2-sulfobenzamido)-2,7-naphthalenedisulfonic acid trisodium salt as a powder.

The above product and 1.0 g of 10% palladium catalyst on carbon in 100 ml of water are hydrogenated for about 1½ hours. The reaction mixture is filtered through diatomaceous earth and the filtrate is diluted to about 500 ml with absolute ethyl alcohol. The dark solid formed is collected by filtration and is taken up in water. Absolute ethyl alcohol is added incrementally with filtration until all of the dark material separates, first as a solid then as an oil. The addition of more absolute ethyl alcohol to the oil results in the formation of a light tan solid which is collected by filtration and dried by conventional means to yield 19.67 g of the product of the example.

EXAMPLE 14

4,4'-{Ureylenebis[(2-sulfo-4,1-phenylenecarbonyl)imino]}di-2,7-naphthalenedisulfonic acid hexasodium salt A 5.68 g portion of the product of Example 13 and 4.24 g of sodium carbonate is dissolved in 50 ml of water. Phosgene gas is passed into the solution until the solution is acidic to Congo red indicator with formation of a solid. The reaction mixture is made basic with 5 N sodium hydroxide and the solid is collected by filtration. The product is recrystallized from water after treatment with activated charcoal and is oven-dried overnight to yield 3.90 g of the product of the example as a solid.

EXAMPLE 15

5-(4-Amino-2-sulfobenzamido)-4-hydroxy-2-naphthalenesulfonic acid disodium salt

An 11.1 g portion of 1-amino-8-naphthol-6-sulfonic acid is dissolved in 100 ml of water and is neutralized to pH 7, then 8.56 g of sodium acetate trihydrate is added with stirring. With stirring being continued, 10.88 g of 4-nitro-2-sulfobenzoic acid anhydride is added all at once. The resulting mixture is stirred for 30 minutes and the residue (4.5 g) is filtered and set aside. The filtrate is acidified with 3.5 ml of concentrated hydrochloric acid and is concentrated. The residue is slurried in water and is filtered. The precipitate is washed with ethyl alcohol and ether and is dried to yield 4.0 g of product a solid. The residue (4.5 g) set aside previously is recycled as above using one-half the amounts of sodium acetate and the mixed anhydride. To the resulting mixture is added a quantity of base sufficient to cause almost complete solution and stirring is continued for 20 minutes. The mixture is filtered and the filtrate is acidified and concentrated to about ½ volume with separation of a solid. This material is collected by filtration, washed with ethyl alcohol and ether, and is dried to give 2.9 g of an orange solid, giving a total yield of 6.9 g of 4-hydroxy-5-(4-nitro-2-sulfobenzamido)-2-naphthalenedisulfonic acid disodium salt.

A 5.12 g portion of the product above is stirred in 250 ml of water, then is filtered. To the filtrate is added 1.0 g of palladium catalyst on charcoal, then the mixture is hydrogenated until no additional hydrogen is absorbed. The mixture is filtered through diatomaceous earth and concentrated. Two crystallizations with ethyl alcohol from aqueous solution yields a total of 4.4 g of the product of the example which is washed with ethyl alcohol and ether and dried.

EXAMPLE 16

5,5'-{Ureylenebis[(2-sulfo-4,1-phenylenecarbonyl)imino]}bis[4-hydroxy-2-naphthalenesulfonic acid]tetrasodium salt Phosgene gas is passed into a solution of 4.1 g of the product of Example 15, and 1.81 g of sodium carbonate in 35 ml of water until it is acidic to Congo red indicator. The cooled solution is adjusted to pH 8 by the addition, with stirring, of more sodium carbonate, then is adjusted to pH 6.5 with acetic acid. The resulting mixture is filtered and concentrated. The residue is dissolved in 40 ml of hot water then is cooled with formation of a precipitate. The product is collected by filtration, is washed with some water, then with ethyl alcohol and ether and is dried by conventional means to yield 1.6 g of the product of the example.

EXAMPLE 17

4-(4-Amino-2-sulfobenzamido)-5-hydroxy-1,7-naphthalenedisulfonic acid trisodium salt Under a nitrogen atmosphere, a 10.9 g portion of (87.4%) 4-amino-5-hydroxy-1,7-naphthalenedisulfonic acid is dissolved in 100 ml of water and is neutralized to pH 7.0 with sodium hydroxide, then 6.45 g of sodium acetate trihydrate is added. An 8.05 g amount of 4-nitro-2-sulfobenzoic acid anhydride is added at one time with stirring, and then stirring is continued for one hour. The reaction mixture is filtered, the filtrate is acidified with 2.2 ml of concentrated hydrochloric acid and is evaporated. The residue is dissolved in 40 ml of hot water and is filtered. To the filtrate is added 160 ml of ethyl alcohol which causes formation of a yellow solid. After stirring for ½ hour, the precipitate is collected by filtration, washed with ethyl alcohol ether and dried in vacuo to yield 8.5 g of material. The filtrate is concentrated and the residue is dissolved in 25 ml of hot water. The solution is filtered and 450 ml of absolute ethyl alcohol is added to the filtrate. The additional precipitated product is collected, washed and dried to yield 7.3 g.

The combined product (15.8 g) is recycled with 2.23 g of sodium acetate and 4.03 g of 4-nitro-2-sulfobenzoic acid anhydride. The reaction mixture filtrate is acidified with 1.1 ml of concentrated hydrochloric acid and is evaporated. The residue is recrystallized twice from water with ethyl alcohol to yield 12.9 g of product. An 11.9 g portion of this material is stirred in 40 ml of N sodium hydroxide for 10 minutes, then is acidified to pH 2 with concentrated hydrochloric acid. To this solution is slowly added 160 ml of ethyl alcohol which causes formation of a yellow precipitate. The precipitate is collected by filtration, washed with 80% aqueous ethyl alcohol, ethyl alcohol and ether and is dried in vacuo to yield 10.5 g of 5-hydroxy-4-(4-nitro-2-sulfobenzamido)-1,7-naphthalenedisulfonic acid trisodium salt.

The product above and 1.0 g of 10% palladium catalyst on carbon in 160 ml of water is hydrogenated as described in Example 7. The reaction mixture is filtered through diatomaceous earth and the filtrate is concentrated. The residue is dissolved in 40 ml of hot water and 100 ml of absolute ethyl alcohol is added. The precipitate formed is collected by filtration, is washed with ethyl alcohol and ether and is dried to yield 4.65 g of the product of the example.

EXAMPLE 18

4,4'-Ureylenebis[(2-sulfo-4,1-phenylenecarbonyl)imino]bis[5-hydroxy-1,7-naphthalenedisulfonic acid]hexasodium salt Phosgene is bubbled into a solution of 4.0 g of the product of Example 17 and 1.56 g of sodium carbonate in 35 ml of water until the mixture is acidic to Congo red indicator. The pH is adjusted to pH 8 with sodium carbonate and then to about pH 6.5 with glacial acetic acid. The solution is evaporated and the residue dissolved in 20 ml of water, the 60 ml of absolute ethyl alcohol is added with separation of an oil. The oil is collected and triturated with ethyl alcohol to yield a yellow solid which is filtered and washed with ethanol and ether, and dried. The material is recycled as above and the product is dissolved in 20 ml of water. The solution is adjusted to pH 4.0 with concentrated hydrochloric acid and 70 ml of ethyl alcohol are added slowly with stirring. The precipitate formed is collected by filtration and is washed with 80% aqueous ethyl alcohol, ethyl alcohol and ether, and is dried to yield 1.6 g of the product of the example as a powder.

EXAMPLE 19

8-(4-Amino-2-sulfobenzamido)-1,6-naphthalenedisulfonic acid trisodium salt

To a solution of 25.0 g of 1-naphthylamine-3,8-disulfonic acid in 100 ml of water is added 20 ml of 5 N sodium hydroxide with stirring. The mixture is warmed on a steambath and diluted with absolute ethyl alcohol to yield a crystalline precipitate. The solid is collected at room temperature and is washed with 75% aqueous ethyl alcohol, ethyl alcohol and ether. The product is dried in vacuo at 110° C. overnight to yield 22.8 g of (87%) 8-amino-1,6-naphthalenedisulfonic acid disodium salt.

To a solution of 21.0 g of the above product and 12.3 g of sodium acetate trihydrate in 180 ml of water at 2° C. (ice-bath) is added 16.5 g of powdered 4-nitro-2-sulfobenzoic acid anhydride with rapid stirring. The mixture is stirred in the ice-bath for a total of 15 minutes, and then is filtered. The filtrate is cooled in an ice bath and acidified with 2.0 ml of concentrated hydrochloric acid, then is promptly diluted with 600 ml of cold ethyl alcohol. The solid so formed is collected by filtration, washed with 85% aqueous ethyl alcohol, ethyl alcohol and ether, and dried in vacuo at 90° C. to give 24.8 g of 8-(4-nitro-2-sulfobenzamido)-1,6-naphthalenedisulfonic acid trisodium salt as a pale tan powder.

A 20.0 g portion of the preceding compound and 1.4 g of 10% palladium catalyst on carbon in 120 ml of distilled water is hydrogenated as described in Example 7. The resulting mixture is filtered through diatomaceous earth and the filtrate is concentrated to about 80 ml. The solution is diluted with 400 ml of absolute ethyl alcohol and vigorous stirring with formation of a solid. The solid is collected by filtration and is triturated with acetone. The material is washed with acetone and dried in vacuo at 110° C. to yield 7.0 g of the product of the example as a yellow solid.

EXAMPLE 20

8,8'-[Ureylenebis(2-sulfo-4,1-phenylenecarbonyl)imino]di-1,6-naphthalenedisulfonic acid hexasodium salt Phosgene gas is bubbled into a solution of a 10.0 g portion of the product of Example 19 (prepared in the manner described) and 4.5 g of anhydrous sodium carbonate in 100 ml of water until the solution becomes acidic to Congo red indicator. The solution is neutralized with sodium carbonate and the excess sodium carbonate is decomposed with acetic acid. The solution is warmed and 150 ml of ethyl alcohol is added which causes formation of a precipitate. The precipitate is collected by filtration, washed with 85% ethyl alcohol, ethyl alcohol and ether and dried in vacuo at 110° C. to yield 8.8 g of the product of the example as a white solid.

EXAMPLE 21

4-(4-Amino-2-sulfobenzamido)-1,6-naphthalenedisulfonic acid trisodium salt

A 50.0 g amount of (61.5%) 1-naphthylamine-4,7-disulfonic acid is dissolved in 150 ml of water and 5 N sodium hydroxide is added until basic pH (10–11). The solution is warmed and ethyl alcohol is added until a precipitate forms. The solid is collected by filtration, washed with 85% ethyl alcohol, ethyl alcohol and ether and is dried in vacuo at 110° C. to give 31.0 g of 4-amino-1,6-naphthalenedisulfonic acid disodium salt.

A 30.0 g portion of the preceding product and 17.5 g of sodium acetate trihydrate is dissolved in 200 ml of water and cooled to 2° C. To this solution is added 24.0 g of 4-nitro-2-sulfobenzoic acid anhydride with vigorous stirring. The mixture is stirred in an ice bath for a total of 15 minutes and the solid formed is collected and washed and dried as previously described to yield 33.5 g of 4-(4-nitro-2-sulfobenzamido)-1,6-naphthalenedisulfonic acid trisodium salt as a tan powder.

A 25.0 g portion of the product above and 1.7 g of 10% palladium catalyst on carbon in 110 ml of water is hydrogenated as described in Example 7. The resulting mixture is filtered through diatomaceous earth, and the filtrate is diluted with 800 ml of absolute ethyl alcohol. The mixture is stirred and cooled with formation of a solid which is collected by filtration. The solid is washed with ethyl alcohol and ether and dried in vacuo at 110° C. to yield 21.0 g of the product of the example as a white solid.

EXAMPLE 22

4,4'-{Ureylenebis[(2-sulfo-4,1-phenylenecarbonyl)imino]}-di-1,6-naphthalenedisulfonic acid hexasodium salt

Phosgene gas is bubbled into a solution of a 12.0 g portion of the product of Example 21 and 5.6 g of anhydrous sodium carbonate in 100 ml of water until the solution becomes acidic to Congo red indicator. The solution is neutralized as described in Example 20, then is warmed and 300 ml of ethyl alcohol is added. An oil separates which solidifies on standing. The solid is collected by filtration and is washed with 85% aqueous ethyl alcohol, ethyl alcohol and ether, then is dried in vacuo at 110° C. to give 11.5 g of the product of the example as a white solid.

EXAMPLE 23

4-(4-Amino-2-sulfobenzamido)-2,6-naphthalenedisulfonic acid trisodium salt

A 45.0 g amount of (62.5%) 1-naphthylamine-3,7-disulfonic acid is suspended in 200 ml of water and 30 ml of 5 N sodium hydroxide is added to it. The solution is warmed and absolute ethyl alcohol is added until a cloudy precipitate forms. The solution is cooled and the solid is collected by filtration and is washed with 85% ethyl alcohol, ethyl alcohol and ether. The product is dried in vacuo at 110° C. to give 21.0 g of 4-amino-2,6-naphthalenedisulfonic acid disodium salt.

To a solution of 10.58 g of the product above and 6.15 g of sodium acetate trihydrate in 90 ml of water at 2° C. is added with vigorous stirring 8.25 g of powdered 4-nitro-2-sulfobenzoic acid anhydride. The mixture is stirred in an ice-bath for a total of 20 minutes and then filtered. The filtrate is cooled in an ice bath, acidified with 2.0 ml of concentrated hydrochloric acid and is diluted with 800 ml of cold ethyl alcohol. The solid so formed is collected and washed and dried as previously described to yield 12.5 g of 4-(4-nitro-2-sulfobenzamido)-2,6-naphthalenedisulfonic acid trisodium salt.

A mixture of 9.5 g of the preceding compound, 1.4 g of 10% palladium catalyst on carbon and 90 ml of water is hydrogenated as described in Example 7. The resulting mixture is filtered through diatomaceous earth and the filtrate is diluted with 600 ml of absolute ethyl alcohol and is cooled. The solid is filtered off and washed with ethyl alcohol and ether, then is dried in vacuo at 110° C. to yield 7.3 g of white solid as the product of the example.

EXAMPLE 24

4,4'-{Ureylenebis[(2-sulfo-4,1-phenylenecarbonyl)imino]}-di-2,6-naphthalenedisulfonic acid hexasodium salt

Phosgene gas is bubbled into a solution of 5.0 g of the product of Example 23 and 2.5 g of anhydrous sodium carbonate in 50 ml of water until the solution becomes acidic to Congo red indicator. The solution is neutralized as described in Example 20, then is warmed and absolute ethyl alcohol is added until a precipitate is formed. The solid is collected and washed with 85% aqueous ethyl alcohol, ethyl alcohol and ether, then is dried in vacuo at 110° C. to yield 4.3 g of the product of the example as a white solid.

EXAMPLE 25

4-(4-Amino-2-sulfobenzamido)-1,5-naphthalenedisulfonic acid trisodium salt

A 14.0 g amount of 4-amino-1,5-naphthalenedisulfonic acid is suspended in 100 ml of water and the solution is made basic with 5 N sodium hydroxide. The solution is warmed and absolute ethyl alcohol is added until a solid is precipitated. The solid is collected by filtration and is washed with 85% aqueous ethyl alcohol, ethyl alcohol and ether, then dried in vacuo to yield 12.0 g of 4-amino-1,5-naphthalenedisulfonic acid disodium salt.

To a solution of 10.5 g of the above material and 6.15 g of sodium acetate trihydrate in 90 ml of water at 2° C. is added 8.25 g of 4-nitro-2-sulfobenzoic acid anhydride with vigorous stirring. The mixture is stirred in an ice-bath for a total of 25 minutes and is filtered. The solid is washed and dried as previously described to yield 13.5 g of 4-(4-nitro-2-sulfobenzamido)-1,5-naphthalenedisulfonic acid trisodium salt as a yellow powder.

A mixture of 9.5 g of the preceding compound, 1.4 g of 10% palladium catalyst on carbon and 90 ml of water is hydrogenated as described in Example 7. The resulting mixture is filtered through diatomaceous earth and the filtrate is diluted with about 800 ml of absolute ethyl alcohol and is cooled. The solid is collected by filtration, washed with ethyl alcohol and ether, then is dried in vacuo to yield 6.5 g of the product of the example as a light orange solid.

EXAMPLE 26

4,4'-{Ureylenebis[(2-sulfo-4,1-phenylenecarbonyl)imino]}-di-1,5-naphthalenedisulfonic acid trisodium salt

Phosgene gas is bubbled into a solution of 5.0 g of the product of Example 25 and 2.5 g of anhydrous sodium carbonate in 60 ml of water until the solution becomes acidic to Congo red indicator. The solution is neutralized as described in Example 20, then is warmed and absolute ethyl alcohol is added until a precipitate is formed. The solid is collected and washed with 85% aqueous ethyl alcohol, ethyl alcohol and ether, then is dried in vacuo at 110° C. to yield 4.0 g of the product of the example as a beige solid.

EXAMPLE 27

5-Amino-N-3,6,8-trisulfo-1-naphthylisophthalamic acid trisodium salt

A mixture of 60.0 g of 5-nitroisophthalic acid, 300 ml of thionyl chloride and one ml of dimethylformamide is stirred at room temperature for 30 minutes and then refluxed for one hour. The resulting clear solution is allowed to stand 24 hours, then is evaporated to a small volume in vacuo. The evaporation step is then repeated with toluene and the resulting liquid is diluted with 250 ml of hexane. The mixture is stirred and cooled until the resulting oil is solidified. The product is ground to a powder and is recrystallized twice from carbon tetrachloride to give 47.4 g of 5-nitroisophthaloyl chloride.

To a solution of 16.0 g of 8-amino-1,3,6-naphthalenetrisulfonic acid trisodium salt and 10.0 g of sodium acetate trihydrate in 100 ml of water is added a solution of 8.7 g of 5-nitroisophthaloyl chloride in 75 ml of diethyl ether and the mixture is stirred vigorously for 40 minutes at room temperature. The layers are separated and the aqueous phase is concentrated in vacuo to approximately 55 ml and diluted with 100 ml of ethanol. After standing overnight, the mixture is filtered and the product is crystallized from 50% aqueous ethanol to give a total of 10.8 g of product as the sum of several crops. The product is dried at 110° C. to give 9.3 g of 5-nitro-N-3,6,8-trisulfo-1-naphthylisophthalamic acid trisodium salt as a yellow powder.

A 9.0 g portion of the preceding product and 1.0 g of 10% palladium catalyst on carbon in 100 ml of water is hydrogenated for 3 hours. The mixture is filtered and the filtrate is concentrated and diluted with ethanol. The mixture is filtered and the product dried at 110° C. to give 8.7 g of 5-amino-N-3,6,8-trisulfo-1-naphthylisophthalamic acid trisodium salt as an off-white powder.

EXAMPLE 28

5,5'-Ureylenebis[N-(3,6,8-trisulfo-1-naphthyl)]isophthalamic acid octasodium salt A solution of 3.8 g of the product of Example 27 and 1.6 g of sodium carbonate in 20 ml of water is treated with phosgene gas at room temperature until the solution is just weakly basic. The excess carbonate is decomposed with acetic acid and the product is precipitated with 100 ml of ethanol. The mixture is filtered and the product is dried at 110° C. to give the product of the example as an off-white powder.

EXAMPLE 29

5-Amino-N-4,6,8-trisulfo-1-naphthylisophthalamic acid methyl ether trisodium salt To a solution of 3.5 g of 8-amino-1,3,5-naphthalenetrisulfonic acid trisodium salt and 2.24 g of sodium acetate trihydrate in 40 ml of water is added, with stirring, 2.0 g of 3-carbomethoxy-5-nitrobenzoyl chloride. Stirring is continued for one hour, then 4.0 ml of ethyl ether is added and stirring is continued for 2 hours longer. The solution is filtered and the filtrate is concentrated. The residue is dissolved in 20 ml of hot water and on addition of 20 ml of absolute ethyl alcohol a precipitate is formed. The precipitate is mobilized with water and is filtered and washed with 80% aqueous ethyl alcohol, ethyl alcohol and ether. The filtrate is allowed to stand overnight to afford additional product which is collected and washed as above. The combined product is dried by conventional means to yield 3.3 g of 5-nitro-N-4,6,8-trisulfo-1-naphthylisophthalamic acid methyl ester trisodium salt.

A 3.27 g portion of the preceding product and 700 mg of 10% palladium catalyst on carbon in 100 ml of water is hydrogenated in a Parr shaker until no more hydrogen is absorbed. The resulting mixture is filtered through diatomaceous earth and the filtrate is evaporated. The residue is dissolved in about 15 ml of hot water and absolute ethyl alcohol is added to a total volume of 250 ml with formation of a precipitate. The precipitate is collected by filtration, washed with ethyl alcohol and ether and dried to yield 2.4 g of the product of the example as a powder.

EXAMPLE 30

5,5'-Ureylenebis[N-(4,6,8-trisulfo-1-naphthyl)isophthalamic acid]dimethyl ester hexasodium salt Phosgene is bubbled into a solution of 2.0 g of the product of Example 29 and 710 mg of sodium carbonate in 20 ml of water, with stirring, until acidic to Congo red indicator. The pH of the solution is adjusted to pH 6.0 with sodium carbonate, then it is filtered and concentrated. The residue is dissolved in 12 ml of hot water and 40 ml of absolute ethyl alcohol is added slowly, with stirring, for ½ hour. The white solid formed is collected and washed with 80% ethyl alcohol, ethyl alcohol and ether, then is dried at 120° C. in an Abderhalden apparatus to yield 1.6 g of the product of the example.

EXAMPLE 31

5-Amino-N-4,6,8-trisulfo-1-naphthylisophthalamic acid trisodium salt

An 8.0 g amount of 5-nitro-N-4,6,8-trisulfo-1-naphthylisophthalamic acid methyl ester trisodium salt (prepared as described in Example 29) and 122 ml of 0.1 N sodium hydroxide is stirred at room temperature for 3 hours. The resulting mixture is acidified to pH 2.0 with dilute hydrochloric acid and is concentrated. The residue is dissolved in 25 ml of hot water and the total volume is brought to 250 ml by the addition of absolute ethyl alcohol with stirring. The precipitate formed is collected and washed with ethyl alcohol and ether, then is oven dried to give 7.0 g of 5-nitro-N-4,6,8-trisulfo-1-naphthylisophthalamic acid trisodium salt.

A 6.0 g portion of the above product and 900 mg of 10% palladium catalyst on carbon in 130 ml of water is hydrogenated as described in Example 29. The resulting mixture is filtered through diatomaceous earth and the filtrate is concentrated. The residue is dissolved in about 20 ml of hot water and ethyl alcohol is added to a total volume of 250 ml with formation of a precipitate. The solid is collected and washed with ethyl alcohol and ether and is dried by conventional means to yield 5.0 g of the product of the example.

EXAMPLE 32

5,5'-Ureylenebis[N-(4,6,8-trisulfo-1-naphthyl)isophthalamic acid]octasodium salt Phosgene gas is bubbled into a solution of 4.0 g of the product of Example 31 and 1.46 g of sodium carbonate in 30 ml of water until acidic to Congo red indicator. The pH of the resulting mixture is adjusted to pH 7.2 with sodium carbonate, then the mixture is filtered. The filtrate is concentrated and the residue is dissolved in 20 ml of hot water, then 70 ml of absolute ethyl alcohol is added slowly, with stirring. The precipitate formed is collected by filtration, washed with 80% aqueous ethyl alcohol, ethyl alcohol and ether and dried in an Abderhalden apparatus to yield 3.0 g of the product of the example as a pink solid.

EXAMPLE 33

3,3'-Ureylenebis{5-[(8-hydroxy-4,6-disulfo-1-naphthenyl)aminocarbonyl]-benzoic acid}tetrasodium salt A solution of 4.0 g of 4-amino-5-hydroxy-1,7-naphthalenedisulfonic acid in 60 ml of water is neutralized to pH 7.2 with NaOH. A 3.6 g portion of sodium acetate trihydrate is added followed by 3.22 g of 3-carbomethoxy-5-nitrobenzoyl chloride with vigorous stirring. The mixture is stirred fro 3 hours, 600 mg of sodium acetate trihydrate and 500 mg of 3-carbomethoxy-5-nitrobenzoyl chloride are added and the mixture is stirred for 2 more hours. A yellow solid is recovered by filtration washed with 50% aqueous ethanol, ethanol, ether and dried giving 2.1 g.

A 570 mg portion of this solid is suspended in 10 ml of 0.1 N sodium hydroxide and stirred overnight. A one ml portion of 1 N sodium hydroxide is added and the mixture is stirred for 20 minutes. The mixture is acidified to pH2 and evaporated. The residue is dissolved in 5 ml of hot water, drilled in an ice box and the solid is collected by filtration, giving 490 mg of N-(8-hydroxy-4,6-disulfo-1-naphthyl)-5-nitroisophthalamic acid disodium salt.

A 4.8 g portion of this 5-nitro compound (prepared in the manner described above) is dissolved in 250 ml of water, filtered and hydrogenated in a Parr shaker with 900 mg of 10% palladium on carbon. The mixture is filtered and the filtrate is evaporated. The residue is dissolved in 25 ml of hot water and ethanol is added to precipitate the desired 5-amino derivative which is collected by filtration, washed with ethanol and ether and dried giving 3.95 g of grey solid.

A 3.9 g portion of the 5-amino derivative is dissolved in 50 ml of water and the pH is adjusted to 7 with sodium carbonate. A 1.63 g portion of sodium carbonate is added and phosgene is passed through the solution until it is acidic to Congo Red. The mixture is readjusted to pH 7 with sodium carbonate, filtered and concentrated. The residue is dissolved in 40 ml of hot water and diluted to 130 ml with ethanol. The mixture is filtered and the solid is washed with 50% aqueous ethanol, ethanol, ether and dried giving 3.2 g of 5,5'-ureylenebis[N-(8-hydroxy-4,6-disulfo-1-naphthenyl)-isophthalamic acid]-hexasodium salt as a yellow solid.

This solid is dissolved in 20 ml of hot water and 35 ml of ethanol is added with stirring. The mixture is filtered and the solid is washed with 50% aqueous ethanol, ethanol, ether and dried. This solid is dissolved in 8 ml of water, acidified to pH 2 and 35 ml of ethanol is added. The solid is collected by filtration, washed with 80% ethanol, ethanol, ether and dried giving the final desired product.

EXAMPLE 34

4,4'-{Ureylenebis[(6-methyl-3,1-phenylenecarbonyl)imino]}-bis[5-hydroxy-1,7-naphthalenedisulfonic acid],tetrasodium salt A 16 g portion of 4-amino-5-hydroxy-1,7-naphthalenedisulfonic acid in 120 ml of water is adjusted to pH 7.2. A 7.6 g portion of sodium acetate trihydrate and 8.8 g of 2-methyl-5-nitrobenzoyl chloride are added with vigorous stirring. The mixture is stirred overnight at room temperature. The solid is then collected by filtration, washed with water, 80% ethanol, ethanol, ether and dried, giving 13.0 g of 5-hydroxy-4-(5-nitro-o-toluamido)-1,7-naphthalenedisulfonic acid, disodium salt.

An 11.0 g portion of the above nitro derivative is 110 ml of dimethylformamide containing 1.25 g of 10% palladium on carbon is shaken in a Parr apparatus until no further hydrogen is taken up. The reaction mixture is filtered and the filtrate is concentrated to a small volume. Ethanol is added to a total volume of 500 ml. The mixture is concentrated to 100 ml and ether is added to precipitate a yellow solid which is collected by filtration, washed with ether and dried giving 7.6 g of the corresponding amino derivative.

A 7.8 g portion of the amino derivative prepared as described above, and 3.4 g of sodium carbonate is dissolved in 150 ml of water. Phosgene is bubbled into the solution with tap water cooling until acidic to Congo Red. The pH is adjusted to 7, and 3.4 g of sodium carbonate is added. Phosgene is passed in until the solution is acidic to Congo Red. The solution is concentrated, and crops are separated as they precipitate. The first crop is washed with 80% ethanol, ethanol, ether and dried giving 1.5 g of solid which is dissolved in 15 ml of water, neutralized with sodium carbonate and precipitated with ether, washed with ethanol and ether and dried. A 500 mg portion of this solid is stirred with 3 ml of 1 N sodium hydroxide at room temperature for 2 hours, acidified and then filtered giving 300 mg of the desired final product.

EXAMPLE 35

8,8'-[Carbonylbis[imino[(-6-sulfo-3,1-phenylene)carbonylimino]]-bis-1,3,6-naphthalenetrisulfonic acid octasodium salt To a solution of 20.0 g of 8-amino-1,3,6-naphthalenetrisulfonic acid trisodium salt and 8.75 g of sodium acetate trihydrate in 180 ml of water at room temperature is added 12.0 g of m-nitrosulfobenzoic anhydride with stirring. A 400 ml portion of water is added. The mixture is stirred at room temperature for 2½ hours and then filtered. The filtrate is cooled, acidified with 2–3 ml of concentrated hydrochloric acid and diluted with ethanol. The pink solid is collected by filtration, washed with 85% ethanol, ether and dried. The filtrate is concentrated to a low volume and diluted with ethanol giving a second crop which is collected and combined with the first crop giving a total of 27.6 g of 8-(5-nitro-2-sulfobenzamido)-1,3,6-naphthalene trisulfonic acid tetrasodium salt.

A mixture of 24.0 g of the above 5-nitro derivative and 2.0 g of 10% palladium on carbon in 60 ml of water is hydrogenated on a Parr shaker at room temperature for one hour. The mixture is filtered. The filtrate is diluted with ethanol. The oil which forms is triturated with ethanol producing a solid which is collected, washed with 85% ethanol, ethanol, ether and dried at 110° C. in vacuo giving the corresponding 5-amino derivative.

A 1.9 g portion of this 5-amino derivative is dissolved in 40 ml of water. A 0.9 g portion of anhydrous sodium carbonate is added and phosgene is bubbled through the solution until it is acidic. The solution is neutralized with anhydrous sodium carbonate and excess sodium carbonate is destroyed by the addition of glacial acetic acid. The mixture is diluted with ethanol. The oil which separates is triturated twice with ethanol producing a solid which is collected, washed with 85% ethanol, ethanol, ether and dried. This solid is recrystallized from water and ethanol giving 700 mg of the desired final product as a white solid.

EXAMPLE 36

8,8'-[Carbonylbis[amino[(-6-sulfo-3,1-phenylene)carbonylimino]]-bis-1,3,6-naphthalenetrisulfonic acid octasodium salt A 6.6 g portion of 8-amino-1,3,6-naphthalenetrisulfonic acid trisodium salt and 2.92 g of sodium acetate trihydrate are dissolved in 180 ml of water at 2° C. A 4.0 g portion of m-nitrosulfobenzoic anhydride is added with stirring. A 400 ml portion of water is added and the mixture is allowed to stand 2½ hours, filtered and the filtrate is cooled, acidified with 2–3 ml of hydrochloric acid and diluted with ethanol. The pink solid is collected by filtration, washed with 85% ethanol, ether and dried giving 2.5 g of 8-(5-nitro-2-sulfobenzamido)-1,3,6-naphthalene trisulfonic acid, tetrasodium salt.

The above product is hydrogenated using 10% palladium on carbon as catalyst to produce 1.9 g of 8-(5-amino-2-sulfobenzamido)-1,3,6-naphthalene trisulfonic acid, tetrasodium salt as a white solid.

A 1.9 g portion of this product is dissolved in 40 ml of water and 0.9 g of anhydrous sodium carbonate is added. Phosgene is bubbled into the solution until it becomes acidic. The solution is neutralized with sodium carbonate, and the excess sodium carbonate is destroyed with glacial acetic acid. Ethanol is added. The oil is separated and triturated twice with ethanol. The solid is collected and washed with 85% ethanol, ethanol, ether and dried. This solid is recrystallized from a mixture of water and ethanol giving 700 mg of the desired final product as a white solid.

EXAMPLE 37

3,3'-(Carbonyldiimino)bis[5-[(8-hydroxy-3,6-disulfo-1-naphthalenyl)aminocarbonyl]]benzoic acid tetrasodium salt A reaction mixture comprising 8.0 g of 1-naphthol-8-amine-3,6-disulfonic acid, 6.1 g of 3-carbomethoxy-5-nitrobenzoyl chloride, 6.8 g of sodium acetate trihydrate and 80 ml of water is stirred for 3 hours, then 1.2 g of sodium acetate trihydrate and 700 mg of 3-carbomethoxy-5-nitrobenzoyl chloride are added, and stirring is continued for 2 additional hours. The mixture is filtered, the filtrate is concentrated and the residue is dissolved in 60 ml of water when ethanol is added. The precipitate is collected, washed with 80% ethanol, ethanol, ether and dried giving 11.9 g of N-(8-hydroxy-3,6-disulfo-1-naphthyl)-5-nitro-isophthalamic acid methyl ester disodium salt.

An 11.2 g portion of the above product is hydrogenated using 2.0 g of 10% palladium on carbon catalyst in 150 ml of water. Filtration and precipitation with ethanol gives 6.8 g of 5-amino-N-(8-hydroxy-3,6-disulfo-1-naphthyl)-isophthalamic acid methyl ester disodium salt.

A mixture of 6.1 g of this product, 2.5 g of sodium carbonate and 60 ml of water is phosgenated until acidic to Congo Red. The pH is adjusted to 7 with sodium carbonate, and 400 ml of ethanol is added with stirring. The solid is separated, washed with ethanol and ether and dried giving 2.8 g of 5,5'-ureylenebis[N(8-hydroxy-3,6-disulfo-1-naphthenyl)]isophthalamic acid dimethyl ester tetrasodium salt.

A 2.5 g portion of this product, 9 ml of 1 N NaOH and 5 ml of water are stirred in a stoppered flask for one hour and then acidified to pH 2. An equal volume of ethanol is added and the solid is collected, washed with 80% ethanol, ethanol, ether and dried giving 2.1 g of the desired final product.

EXAMPLE 38

3,3'-Ureylenebis[5-(8-hydroxy-4,6-disulfo-1-naphthenyl)aminocarbonyl]benzoic acid tetrasodium salt A mixture of 4.0 g of 1-naphthol-8-amine-3,5-disulfonic acid in 60 ml of water under nitrogen is neutralized to pH 7.2 with sodium hydroxide. A 3.6 g portion of sodium acetate trihydrate is added followed by 3.22 g of 3-carbomethoxy-5-nitrobenzoyl chloride with vigorous stirring. The mixture is stirred for 3 hours, 600 mg of sodium acetate trihydrate and 500 mg of 3-carbomethoxy-5-nitrobenzoyl chloride are added and stirring under nitrogen is continued for 2 more hours. The solid is collected, washed with 50% aqueous ethanol, ethanol, ether and dried giving 2.1 g of solid. A 570 mg portion of this solid is suspended in 10 ml of 0.1 N sodium hydroxide and stirred overnight. A one ml portion of 1 N sodium hydroxide is added and the mixture is stirred for 20 minutes. The mixture is acidified to pH 2, concentrated and the residue is dissolved in 5 ml of hot water. The solution is chilled producing 490 mg of N-(8-hydroxy-4,6-disulfo-1-naphthenyl)-5-nitro-isophthalamic acid disodium salt as a yellow solid.

A 4.8 g portion of N-(8-hydroxy-4,6-disulfo-1-naphthenyl)-5-nitro-isophthalamic acid disodium salt, prepared as described above is dissolved in 250 ml of water, filtered and the filtrate is hydrogenated with 900 mg of 10% palladium on carbon as catalyst. The reaction mixture is filtered. The filtrate is evaporated, and the residue is dissolved in 25 ml of hot water. Ethanol is added, the solid is collected, washed with ethanol, ether and dried, giving 3.95 g of 5-amino-N-(8-hydroxy-4,6-disulfo-1-naphthenyl)-isophthalamic acid disodium salt.

A 3.9 g portion of the above amine in 50 ml of water is adjusted to pH 7 with sodium carbonate. A 1.63 g portion of sodium carbonate is added and the mixture is phosgenated until acidic to Congo Red. The pH is adjusted to 7 with sodium carbonate. The mixture is filtered. The filtrate is concentrated and the residue is dissolved in 40 ml of hot water. Ethanol is added to a total volume of 130 ml. The solid is collected, washed with 80% aqueous ethanol, ethanol, ether and dried giving 3.2 g of 3,3'-ureylenebis[5-(8-hydroxy-4,6-disulfo-1-naphthenyl)aminocarbonyl]benzoic acid tetrasodium salt.

This material is dissolved in 20 ml of hot water. A 35 ml portion of ethanol is added with stirring. The precipitate is removed by filtration. The filtrate yields a second crop which is collected, washed and dried giving 800 mg. This 800 mg is dissolved in 8 ml of water, acidified to pH 2 and 35 ml of ethanol is added. The resulting solid is collected, washed with 80% ethanol, ethanol, ether and dried giving 700 mg of the desired final product.

EXAMPLE 39

8,8'-[Carbonylbis[imino[(-6-sulfo-3,1-phenylene)carbonylimino]]bis-1,4,6-naphthalenetrisulfonic acid octasodium salt In the manner described in Example 36, treatment of 13.47 g of 8-amino-1,4,6-trisulfonic acid trisodium salt, 6.1 g of sodium acetate trihydrate and 8.23 g of m-nitrosulfobenzoic anhydride in water gives 14 g of 8-(5-nitro-2-sulfobenzamido)-1,4,6-naphthalene trisulfonic acid, tetrasodium salt.

The above is hydrogenated with 10% palladium on carbon to produce 11.3 g of 8-(5-amino-2-sulfobenzamido)-1,4,6-naphthalene trisulfonic acid as a pink solid.

Treatment of this product with phosgene as previously described in Example 36 gives the title compound.

EXAMPLE 40

| Preparation of Compressed Tablet | |
|---|---|
| Ingredient | mg/Tablet |
| Active Compound | 0.5–500 |
| Dibasic Calcium Phosphate N.F. | qs |

| Preparation of Compressed Tablet | |
|---|---|
| Ingredient | mg/Tablet |
| Starch USP | 40 |
| Modified Starch | 10 |
| Magnesium Stearate USP | 1-5 |

EXAMPLE 41

| Preparation of Compressed Tablet - Sustained Action | |
|---|---|
| Ingredient | mg/Tablet |
| Active Compound as Aluminum Lake*, Micronized | 0.5-500 (as acid equivalent) |
| Dibasic Calcium Phosphate N.F. | qs |
| Alginic Acid | 20 |
| Starch USP | 35 |
| Magnesium Stearate USP | 1-10 |

*Complement inhibitor plus aluminum sulfate yields aluminum complement inhibitor. Complement inhibitor content in aluminum lake ranges from 5-30%.

EXAMPLE 42

| Preparation of Hard Shell Capsule | |
|---|---|
| Ingredient | mg/Capsule |
| Active Compound | 0.5-500 |
| Lactose, Spray Dried | qs |
| Magnesium Stearate | 1-10 |

EXAMPLE 43

| Preparation of Oral Liquid (Syrup) | |
|---|---|
| Ingredient | % W/V |
| Active Compound | 0.05-5 |
| Liquid Sugar | 75.0 |
| Methyl Paraben USP | 0.18 |
| Propyl Paraben USP | 0.02 |
| Flavoring Agent | qs |
| Purified Water qs ad | 100.0 |

EXAMPLE 44

| Preparation of Oral Liquid (Elixir) | |
|---|---|
| Ingredient | % W/V |
| Active Compound | 0.05-5 |
| Alcohol USP | 12.5 |
| Glycerin USP | 45.0 |
| Syrup USP | 20.0 |
| Flavoring Agent | qs |
| Purified Water qs ad | 100.0 |

EXAMPLE 45

| Preparation of Oral Suspension (Syrup) | |
|---|---|
| Ingredient | % W/V |
| Active Compound as Aluminum Lake, Micronized | 0.05-5 (acid equivalent) |
| Polysorbate 80 USP | 0.1 |
| Magnesium Aluminum Silicate, Colloidal | 0.3 |
| Flavoring Agent | qs |
| Methyl Paraben USP | 0.18 |
| Propyl Paraben USP | 0.02 |
| Liquid Sugar | 75.0 |

| Preparation of Oral Suspension (Syrup) | |
|---|---|
| Ingredient | % W/V |
| Purified Water qs ad | 100.0 |

EXAMPLE 46

| Preparation of Injectable Solution | |
|---|---|
| Ingredient | % W/V |
| Active Compound | 0.05-5 |
| Benzyl Alcohol N.F. | 0.9 |
| Water for Injection | 100.0 |

EXAMPLE 47

| Preparation of Injectable Oil | |
|---|---|
| Ingredient | % W/V |
| Active Compound | 0.05-5 |
| Benzyl Alcohol | 1.5 |
| Sesame Oil qs ad | 100.0 |

EXAMPLE 48

| Preparation of Intra-Articular Product | |
|---|---|
| Ingredient | Amount |
| Active Compound | 2-20 mg |
| NaCl (physiological saline) | 0.9% |
| Benzyl Alcohol | 0.9% |
| Sodium Carboxymethylcellulose | 1-5% |
| pH adjusted to 5.0-7.5 | |
| Water for Injection qs ad | 100% |

EXAMPLE 49

| Preparation of Injectable Depo Suspension | |
|---|---|
| Ingredient | % W/V |
| Active Compound | 0.05-5 (acid equivalent) |
| Polysorbate 80 USP | 0.2 |
| Polyethylene Glycol 4000 USP | 3.0 |
| Sodium Chloride USP | 0.8 |
| Benzyl Alcohol N.F. | 0.9 |
| HCl to pH 6-8 | qs |
| Water for Injection qs ad | 100.0 |

We claim:
1. A compound of the formula:

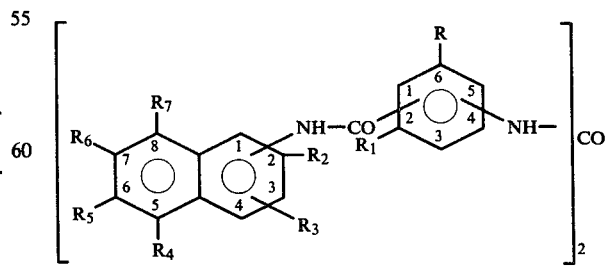

wherein R is COOY, wherein Y is selected from the group consisting of hydrogen, alkali metal and $C_1$-$C_6$ alkyl; $R_1$ is hydrogen; $R_4$, $R_5$ and $R_6$ are selected from the group consisting of hydrogen and SO₃X, wherein X is alkali metal; $R_2$ is hydrogen; with the proviso that there is no $R_1$ or $R_2$ substituent when the bridgehead carbonylimino is attached at the carbon 2-position of the respective ring; with the further proviso that each naphthalene moiety must contain two or three SO₃X substituents, wherein X is as previously defined; $R_3$ is selected from the group consisting of hydrogen, SO₃X and COOY, wherein X and Y are as previously defined; $R_7$ is selected from the group consisting of hydrogen, hydroxy and SO₃X, wherein X is as previously defined; and other pharmaceutically acceptable salts thereof.

2. A compound according to claim 1, wherein R, $R_1$, $R_2$, $R_3$, $R_4$, $R_5$ and $R_6$ are as previously defined; and $R_7$ is selected from the group consisting of SO₃X, wherein X is as previously defined.

3. A compound according to claim 1, wherein R, $R_1$, $R_2$, $R_3$, $R_4$, $R_5$ and $R_6$ are as previously defined; and $R_7$ is selected from the group consisting of hydroxy and hydrogen.

4. The compound according to claim 1, 5,5'-ureylenebis[N-(3,6,8-trisulfo-1-naphthyl)]isophthalamic acid octasodium salt.

5. The compound according to claim 1, 5,5'-ureylenebis[N-(4,6,8-trisulfo-1-naphthyl)isophthalamic acid]dimethyl ester hexasodium salt.

6. The compound according to claim 1, 5,5'-ureylenebis[N-(4,6,8-trisulfo-1-naphthyl)isophthalamic acid]octasodium salt.

7. The compound according to claim 1, 3,3'-ureylenebis[5-[(8-hydroxy-4,6-disulfo-1-naphthyl)carbamoyl]benzoic acid]tetrasodium salt.

8. The compound according to claim 1, 3,3'-(carbonyldiimino)bis[5-[(8-hydroxy-3,6-disulfo-1-naphthalenyl)aminocarbonyl]]benzoic acid tetrasodium salt.

* * * * *